US010426969B2

(12) United States Patent
Rohan

(10) Patent No.: US 10,426,969 B2
(45) Date of Patent: Oct. 1, 2019

(54) MAGNETIC FIELD STIMULATION

(71) Applicant: The McLean Hospital Corporation, Belmont, MA (US)

(72) Inventor: Michael Rohan, Belmont, MA (US)

(73) Assignee: The McLean Hospital Corporation, Belmont, MA (US)

( * ) Notice: Subject to any disclaimer, the term of this patent is extended or adjusted under 35 U.S.C. 154(b) by 7 days.

(21) Appl. No.: 15/678,617

(22) Filed: Aug. 16, 2017

(65) Prior Publication Data

US 2017/0340894 A1    Nov. 30, 2017

Related U.S. Application Data

(62) Division of application No. 14/347,284, filed as application No. PCT/US2012/057551 on Sep. 27, 2012, now Pat. No. 9,737,726.

(60) Provisional application No. 61/539,877, filed on Sep. 27, 2011, provisional application No. 61/539,893, filed on Sep. 27, 2011.

(51) Int. Cl.
*A61N 2/02* (2006.01)
*A61N 2/00* (2006.01)
*A61N 1/40* (2006.01)

(52) U.S. Cl.
CPC .............. *A61N 2/02* (2013.01); *A61N 1/40* (2013.01); *A61N 2/006* (2013.01)

(58) Field of Classification Search
CPC ............. A61N 1/40; A61N 2/006; A61N 2/02
See application file for complete search history.

(56) References Cited

U.S. PATENT DOCUMENTS

| 5,470,846 A * | 11/1995 | Sandyk | A61K 31/122 |
| | | | 514/159 |
| 7,087,008 B2 * | 8/2006 | Fox | A61N 2/02 |
| | | | 600/13 |
| 2010/0019764 A1 * | 1/2010 | Zahn | G01R 33/34046 |
| | | | 324/309 |
| 2011/0184223 A1 * | 7/2011 | Peterchev | A61N 2/006 |
| | | | 600/14 |

OTHER PUBLICATIONS

Canadian Examination Report dated Jul. 4, 2019, for Application No. 2887370, 5 pages.

* cited by examiner

*Primary Examiner* — Christine H Matthews
*Assistant Examiner* — Joshua Daryl D Lannu
(74) *Attorney, Agent, or Firm* — Goodwin Procter LLP

(57) ABSTRACT

A magnetic coil system featuring a multi-layer structure, a spherical shape, or both allows for efficient generation of a gradient magnetic field that induces an electric field in air in a region proximate to the coil. By subjecting at least a portion of a person's brain to the induced electric field various psychiatric disorders can be treated.

21 Claims, 17 Drawing Sheets

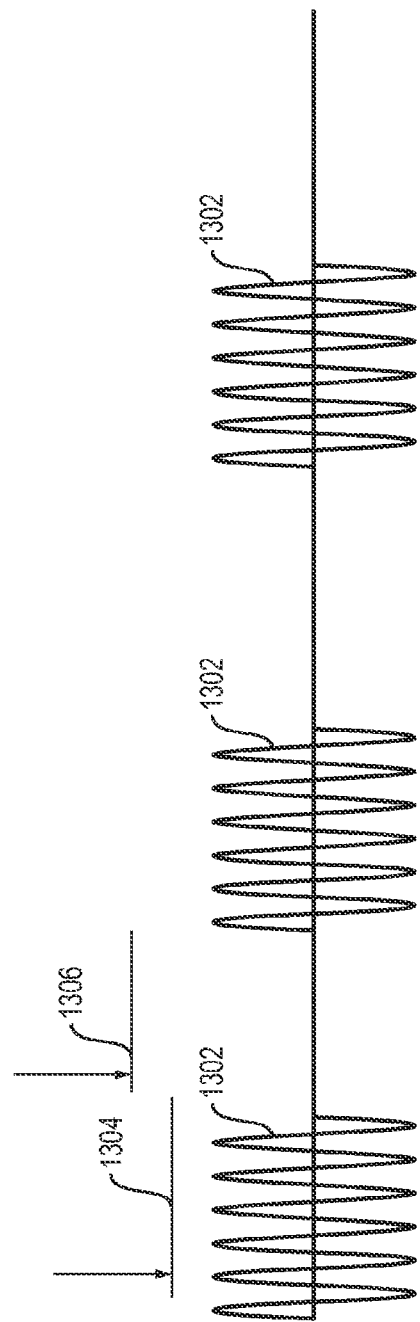

MAGNETIC FIELD STIMULATION

CROSS REFERENCE TO RELATED APPLICATIONS

This application is a division of U.S. patent application Ser. No. 14/347,284, titled "Magnetic Field Stimulation," filed Mar. 26,2014, which is the national stage of international (PCT)Application No PCT/US2012/057551, filed on Sep. 27,2012, and published under PCT Article 21(2)in English, which claims priority claims priority to and benefit of U.S. Provisional Patent Application No. 61/539,877 titled "Low Field Magnetic Stimulation," filed on Sep. 27, 2011, and U.S. Provisional Patent Application No. 61/539,893 also titled "Low Field magnetic Stimulation" and filed on Sep. 27, 2011, each of which is incorporated herein by reference in its entirety.

BACKGROUND OF THE INVENTION

The present invention relates generally to a system and method of induced electric fields and, more particularly, to a system that provides induced electric fields that interact with the brain.

Psychiatric conditions are predominantly treated with pharmaceutical agents. For example existing treatment approaches for depression in bipolar disorder and in major depressive disorder utilize primarily pharmacologic agents, such as selective serotonin reuptake inhibitors and other antidepressant drugs. These agents can be of limited efficacy and may have objectionable side effects.

Repetitive transcranial magnetic stimulation (rTMS) has been used with the goal of treating depression, (see, e.g., George et al., The Journal of Neuropsychiatry and Clinical Neurosciences, 8:373, 1996; Kolbinger et al., Human Psychopharmacology, 10:305, 1995), bipolar disease and other psychiatric conditions. The success of rTMS in the treatment of depression has been varied and has been described in a recent review as "often statistically significant [but] below the threshold of clinical usefulness" (see Wassermann E M, Lisanby S H: Therapeutic application of repetitive transcranial magnetic stimulation: a review. ClinNeurophysiol 2001; 112:1367-1377). Furthermore, rTMS treatment can be unpleasant, with some patients declining participation due to scalp pain induced by the apparatus (George M S, Nahas Z, Molloy M, Speer A M, Oliver N C, Li X B, Arana G W, Risch S C, Ballenger J C: A controlled trial of daily left prefrontal cortex TMS for treating depression. BiolPsychiatry 2000; 48:962-970). The rTMS treatment also carries a small risk of seizure (Wassermann E M: Risk and safety of repetitive transcranial magnetic stimulation: report and suggested guidelines from the International Workshop on the Safety of Repetitive Transcranial Magnetic Stimulation, Jun. 5-7, 1996. Electroencephalogr Clin Neurophysiol 1998; 108:1-16).

Alternative techniques have been described for the treatment of psychiatric disease using low field strength, high repetition rates, and uniform magnetic gradients (U.S. Pat. Nos. 7,033,312 and 6,572,528, and U.S. patent application Ser. No. 11/580,272). Each of these patents and patent applications is incorporated herein by reference in its entirety. Time-varying magnetic fields were used for the purpose of enhancing brain function and for treating various symptoms of depression, anxiety, affective disorders, bipolar disorder, post-traumatic stress disorder, and obsessive compulsive disorder.

Magnetic fields have also been used in Magnetic Resonance Imaging (MRI) systems. These systems use a coil to generate a magnetic field in air to which a portion of a subject's body can be exposed for imaging. A typical MRI coil is a full coil having four elements, such as that depicted in FIG. 5. The desired magnetic field is typically produced in a region in the middle of the coil—a region that is approximately equidistant from all four elements. Using MRI coils for treatment has several disadvantages, however, as described below.

One significant limitation on the use of an MRI gradient coil is its physical size, as imposed by the system, by power concerns, and by the patient. First, the larger the gradient coil, the larger its inductance, and the more the required power to operate the coil. A big coil usually requires more expensive amplifiers, and may impose power switching requirements that cannot be addressed merely by coil design. The portion of the patient which will be imaged must fit inside the coil, which imposes a lower limit on size. This is a limitation on minimum inner diameter of the gradient coil.

Second, the MRI coil fits inside the magnet. The cost and the difficulty in engineering required to make magnet both increase with the increase of the inner diameter of an MRI magnet. A MRI magnet must be large enough to accommodate a patient and the gradient coil within its inner diameter. A typical inner diameter of an MRI magnet must be large enough (e.g., about 90 cm) to provide an adequate opening so that the patient can be located at or near the region where the coil produces the desired magnetic field. This places an upper limit on gradient coil outer diameter.

An MRI gradient coil assembly typically contains 6 elements of gradient coils, two each for the X, Y and Z magnetic field gradient directions. A gradient coil assembly also usually contains resistive shim coils, and cooling for the resistive heat generated by the different coils. All of these items must fit within the inner and outer diameter limits imposed on the coil assembly by the patient access and the magnet size and cost.

In MRI systems, there is a need to cool the resistive heating that is generated inside the coil during operation—most systems need to have water or liquid cooling, because the coil is tightly packed between the inner and outer size limitations. Second, there is magnetic force on the wires in the coil when they have current in them; this causes a net force, usually in the form of a torque that can cause the coil to move.

In MRI systems, the dynamic magnetic fields are reflected from the surrounding magnet and would interfere with the desired target magnetic gradient fields. To prevent this, each gradient coil {X, Y, Z} is designed as a pair of coils—an inner coil and an outer coil—with the outer coil providing an active shield that prevents the gradient magnetic field from reaching the main MRI magnet. Thus, the outer coil merely prevents the magnet from interfering with the field produced by the inner coil.

A gradient coil that only surrounds a patient's head can have a smaller inner diameter, and as a result, may require less power and less cooling. The standard configuration of an MRI coil (i.e., the full coil having four elements as shown in FIG. 5), however, requires a length of coil to extend below the imaging area, i.e., the head. Put another way, the head must be positioned in the middle of the coil. Therefore, the coil must be large enough to accommodate shoulders of the person to be treated. Moreover, typical small-diameter coils do not have a strong mechanical mounting as that of the body coil, and hence, have a greater risk of movement from torque. This poses risk of severe patient injury. Finally, even though the MRI coils that have a relatively small diameter require less power, they still require cooling systems.

There was an attempt to address the shoulder access problem by several designs proposed in the 1990s. These designs used only a "half-coil" design. In this case, the half-coil reduces the extent of the coil below the imaging spot by cutting the coil in half, resulting in reduced gradient field homogeneity but allowing full access to the head, without requiring the person's shoulders to be surrounded by the coil. Such MRI coils, however, had significant torque and they were not safe for patient use. Also, the reduced gradient field homogeneity was not adequate for imaging purposes. The various issues relating to the use of MRI half coils are discussed, for example, in U.S. Pat. No. 5,177,442 to Roemer (describing half coil as having torque (as described by Kondo)); U.S. Pat. No. 5,278,504 to Patrick (describing an asymmetric coil which is not a half coil, in order to eliminate torque); and U.S. Pat. No. 5,793,209 to Kondo (classifying certain coils as effective in imaging but having a torque problem, and certain other coils as effective in torque mitigation but having imaging problems).

Therefore, there is a need for improved apparatuses, systems and methods for treatment of brain using electromagnetic radiation which overcomes the disadvantages and limitations of the prior MR apparatuses and systems discussed above.

SUMMARY OF THE INVENTION

Various embodiments of the present invention feature systems for the induction of electric fields in air. These systems are smaller in size and less bulky compared to previously known coils and may generate less heat. In some embodiments, this is achieved, in part, by employing a coil that has at least one element having two layers, so as to decrease the overall resistance of the coil, which in turn can decrease the heat generated by the coil when compared with conventional coils. Additionally or in the alternative, in some embodiments, the coil includes only one or two elements that are cylindrical, spherical, flat, or bent in shape. Such a coil can induce the electric field outside the region enclosed by the coil, such that the patient's head need not be surrounded by the coil, which can increase patient comfort and simultaneously allows the coil size to be smaller than a coil that surrounds the patient's head. Various embodiments also feature a method of treatment by generating a varying aggregate magnetic field using a coil having one or more elements. The varying magnetic field induces an electric field in air, and a patient's brain is disposed within the region in which the field is induced for the treatment of disorders and/or the enhancement of brain function.

The delivery of these induced electric fields fall into the class of low-field magnetic stimulation (LFMS) techniques. Various embodiments of coils according to the present invention avoid one or more of the problems associated with the MRI coils described above. The invention does not utilize a constant magnetic field, and so there is no magnet such as is found in MRI systems and no size limitations imposed by the magnet, nor requirements for torque free design since there is no magnetic field to provide the torque. Second, the invention requires only one gradient field, and so two gradient coils sets and any resistive shim coils can be eliminated.

The coil module includes a coil and an optional housing for the coil. The coil includes one or more elements, each of which generates a magnetic field that induces a target electric field in air, and a subject's brain can be disposed in the region where the electric field is induced. A coil may have one or more elements that are disposed on a single surface in a non-overlapping manner. Any element may have one, two or more layers to provide reduction of resistive heating as compared to use of a single element. In one embodiment, the coil has a single element that is arranged on a circular or elliptic cylindrical surface having a first radial direction, a second radial direction, and a longitudinal direction. The dimensions of the coil along the first and second radial directions may have the same value. Such an embodiment facilitates relatively easy and/or cheap manufacturing of the coil.

In some embodiments, the coil induces an electric field in a region that is proximate to the volume enclosed by the coil. This can be achieved using a half coil design, i.e., using a coil that has two elements. This allows the coil size to be smaller than that of an MRI coil. In the region proximate to the volume enclosed by the coil, the induced electric field is not sufficiently homogeneous for imaging in an MRI system (e.g., uniformity within 5%-10%), but the homogeneity is adequate for treatment purposes. The coil elements in such a coil can have a surface that is cylindrical, spherical, rectangular, flat, or bent in shape. In various embodiments the coil does not need liquid cooling. In some embodiments, a coil element includes two or more layers of conductors, further decreasing the heat generated by the coil.

Accordingly, in one aspect embodiments of the present invention feature a system for efficiently inducing an electric field. The system includes a pulse generator and a magnetic coil. The magnetic coil has at least one element (e.g., a first element). The first element includes at least two layers—a first layer having an interior surface and an exterior surface, and a second layer having an interior surface and an exterior surface such that the interior surface of the second layer is separated from the exterior surface of the first layer by a distance. The first and second layers are in electrical communication with the pulse generator and are adapted to produce respective first and second magnetic fields. The first and second layers are positioned such that the first and second magnetic fields combine to produce an aggregate magnetic field having a field strength greater than either the first or second magnetic field.

In some embodiments, the distance between all points of the interior surface of the second layer and all corresponding points of the exterior surface of the first layer is within a tolerance threshold. The tolerance threshold, for example, may be about 25% or 10% or 5% of a median distance between the two surfaces. In some embodiments, the distance between the first and second layers is less than about 5 millimeters. The interior surface of the first element may be either a curved surface or a segmented surface having at least two segments at an angle with respect to one another. The first layer of the first element may include a pattern cut in a metal surface or wound wire. The wound wire can be a solid wire, a stranded wire, or a stranded, insulated litz wire. The first layer of the first element may include a number of turns of a conductor, such as a wound wire or a pattern cut in a metal surface. At least one pair of adjacent turns of the conductor may be spaced apart and the several turns may be distributed over the entire first layer. In some embodiments, the distance between the two layers is selected such that the aggregate magnetic field is produced in a region proximate to the magnetic coil. In addition, or alternatively, the first and second layers may be configured such that each layer generates less than about 50 W of heat.

In some embodiments, the first element includes a third layer having an interior surface and an exterior surface, and the interior surface of the third layer is separated from the exterior surface of the second layer by a distance. The third layer produces a third magnetic field that combines with the first and second magnetic fields to produce an aggregate magnetic field having a field strength greater than the aggregate magnetic field produced by the first and second magnetic fields.

The magnetic coil may also include a second element such that an inner surface of the second element and the inner surface of the first element form separate portions of a single surface. In some embodiments, the single surface is the outer surface of a cylinder having a diameter of about 14 inches, and the second element includes two layers. Each of the first and second layers of the first element, and each of the two layers of the second element include a spiral pattern.

One embodiment features a method of treating a psychiatric disorder or enhancing brain function using the system having a two-layer coil element, described above. The method includes supplying electric power to the magnetic coil via the pulse generator so as to produce the aggregate magnetic field. The aggregate magnetic field may induce an electric field in air proximate to the coil. The method also includes disposing a subject relative to the magnetic coil such that at least a portion of the subject's head is located in a region where the electric field is induced. The psychiatric disorder may include one or more of mood disorder, depression, stress and anxiety, schizophrenia, post-traumatic stress disorder (PTSD), and obsessive-compulsive disorder (OCD). The subject may be disposed in either a supine position or a seated position.

In another aspect, various embodiments of the present invention feature a system that can improve patient comfort. The system includes a pulse generator and a magnetic coil. The magnetic coil has a first element and an inner surface of the first element forms at least a part of a spherical surface. The first element is in electrical communication with the pulse generator. A parameter of the magnetic coil may be selected such that the coil produces a gradient magnetic field proximate to a region at least partially enclosed by the spherical surface. The parameter is selected such that the gradient magnetic field can induce an electric field in air up to about 50 V/m. The coil parameter may be one of a radius of the spherical surface, a polar angle of a coil segment, and an azimuth angle of the coil segment.

In some embodiments, the magnetic coil includes a second element, and an inner surface of the second element and the inner surface of the first element form separate portions of the spherical surface. The first element may include a first layer having an interior surface and an exterior surface, and a second layer having an interior surface and an exterior surface. The interior surface of the second layer may be separated from the exterior surface of the first layer by a distance. The distance between all points of the interior surface of the second layer and all corresponding points of the exterior surface of the first layer may be within a tolerance threshold. The tolerance threshold, for example, may be about 25% or 10% or 5% of a median distance between the two surfaces. In some embodiments, the first element includes a number of turns of a conductor, such as a wound wire or a pattern cut in a metal surface. At least one pair of adjacent turns of the conductor may be spaced apart and the several turns may be distributed over the entire first element.

One embodiment features a method of treating a psychiatric disorder or enhancing brain function using the system in which the inner surface of the first element forms at least a part of a spherical surface, as described above. The method includes supplying electric power to the magnetic coil via the pulse generator so as to produce the aggregate magnetic field. The aggregate magnetic field may induce an electric field in air proximate to the coil. The method also includes disposing a subject relative to the magnetic coil such that at least a portion of the subject's head is located in a region where the electric field is induced. The psychiatric disorder may include one or more of mood disorder, depression, stress and anxiety, schizophrenia, PTSD, and OCD. The subject may be disposed in either a supine position or a seated position.

In another aspect, various embodiments of the present invention feature a method of treatment using an induced an electric field. The method includes controlling a pulse generator during a first interval to produce a gradient magnetic field using a coil. The gradient magnetic field has a magnitude that increases at a first rate during the first interval. The pulse generator is controlled during a second interval that is substantially longer than the first interval, such that the magnitude of the magnetic field decreases during the second interval at a second rate substantially smaller than the first rate. As such, an electric field having a magnitude greater than zero is induced in air during the first interval and an electric field of a negative magnitude is induced in air during the second interval. The pulse generator is controlled such that an electric field integrated over a period comprising the first and second intervals is substantially zero. The above steps may be repeated alternately. The method also includes disposing a subject relative to the coil such that at least a portion of the subject's head is located in a region where the electric field is induced. A repetition of the electric field having a magnitude greater than zero may form a series of electric field pulses. A frequency of that series of pulses may be at least 100 Hz.

In some embodiments, the portion of the subject's brain that is located in the region where the electric field is induced includes at least a portion of cortical surface of the subject's brain. The treatment may include enhancing brain function or treating a psychiatric disorder, and the psychiatric disorder can be one or more of mood disorder, depression, stress and anxiety, schizophrenia, PTSD, and OCD. The subject may be disposed in either a supine position or a seated position.

In another aspect, various embodiments of the present invention feature a method of treatment using an induced electric field. The method includes controlling a pulse generator during a first interval to produce a gradient magnetic field using a coil. The pulse generator is controlled such that the gradient magnetic field induces several consecutive sinusoidal electrical pulses having substantially constant amplitude in air during the first interval. The pulse generator is controlled during a second interval such that the gradient magnetic field induces an electric field of substantially zero magnitude in air during the second interval. These steps are repeated in an alternating manner. The method also includes disposing a subject relative to the coil such that at least a portion of the subject's head is located in a region where the several consecutive sinusoidal pulses are induced. A frequency of the consecutive sinusoidal pulses may be greater than about 100 Hz.

The subject may be disposed relative to the coil such that at least a portion of cortical surface of the subject's brain is located in a region where the sequence of sinusoidal pulses is induced. In some embodiments, the treatment includes enhancing brain function or treating a psychiatric disorder.

The psychiatric disorder may include one or more of mood disorder, depression, stress and anxiety, schizophrenia, PTSD, and OCD. The subject may be disposed in either a supine position or a seated position.

BRIEF DESCRIPTION OF THE DRAWINGS

The drawings illustrate embodiments presently contemplated for carrying out the invention. In the drawings:

FIG. 13 shows a pulse pattern with 3 bursts of 12 sine pulses each.

DESCRIPTION OF PREFERRED EMBODIMENTS

Figure 1:
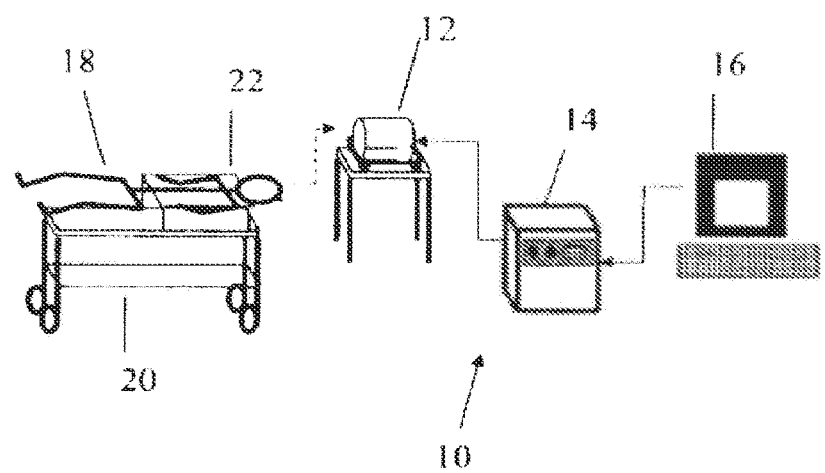
FIG. 1 is a schematic showing the components of the system.

A device 10 according to an embodiment of the present invention is shown in FIG. 1. The device 10 has a magnetic coil module 12, an amplifier 14, and a waveform generator 16. The waveform generator 16 (e.g., a general-purpose programmable computer or a purpose-built electric circuit) provides an electrical pulse sequence to the amplifier 14, which amplifies the electrical signals and provides them to the magnetic coil 12. The coil 12 produces a magnetic field in response to the electrical signals received from the amplifier 14. If the electrical signals vary in time, the magnetic field typically induces an electric field in air.

Figure 2:
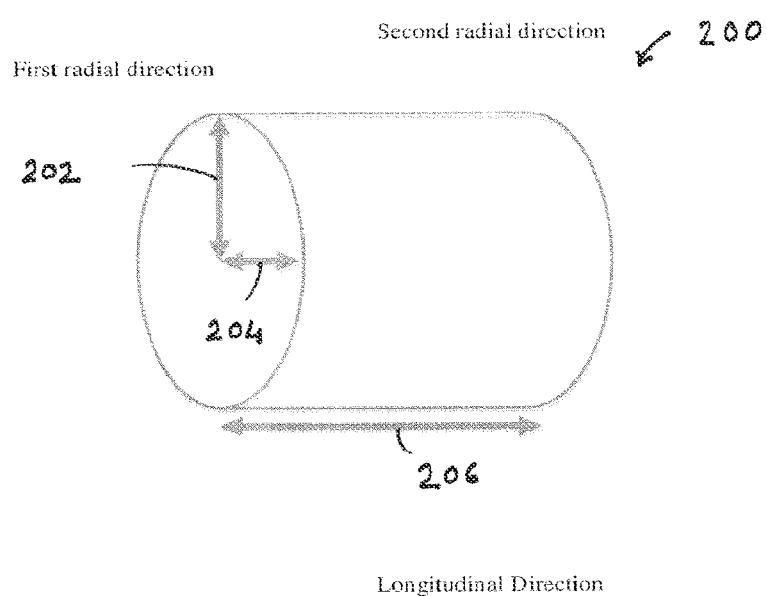
FIG. 2 shows an optional cylindrical structure for supporting coil elements.

The coil module in various embodiments of an LFMS device according to the present invention includes a coil and a housing for the coil. The coil includes one or more elements, each of which generates a magnetic field that may induce a target electric field in air, and a subject's brain can be disposed in the region where the electric field is induced. Typically, the coil has one or more elements that are disposed in a non-overlapping manner, but in some embodiments the elements are located with respect to each other such that they partially overlap. FIG. 2 depicts a structure 200 over or within which the elements of the magnetic coil may be disposed. The structure 200 is a cylinder and has first and second radial directions 202, 204, respectively, and a longitudinal direction 206. A magnetic field may be produced in which any vector component of that field may be produced with a linear gradient in one of these three directions, provided that the remaining vector components of the field satisfy Maxwell's equations. The structure 200 may have other shapes (e.g., spherical, ellipsoidal, etc.), and it may even be flat. In fact, the structure 200 is optional, i.e., the coil elements may be configured to form a magnetic coil without using a separate structure upon which those elements are disposed.

Reducing Heat Dissipation Using a Multi-Layer Coil

The coils in various embodiments may use a significant amount of electrical current in order to provide the required magnetic field. The coil in each of these embodiments will undergo resistive heating during operation, and the coil will increase in temperature until the heat lost through cooling equals the heat generated during operation. Because the coil is in close proximity to the patient during device operation, heating must be limited for patient comfort and safety. In addition, reducing heat generation by the coil allows for a wider range of materials to be used as part of the coil and coil housing due to the lower operating temperature, facilitating easier and less expensive manufacturing.

Cooling is performed through conductive means (radiative cooling at room temperature is not significant). Typical cooling methods for a conventional coil include liquid cooling or air cooling. Liquid cooling is very effective but adds system cost, maintenance cost, and the risk of on-site malfunction to the device. Air cooling requires no additional cost or subsystem but is limited to the order of 60 W power levels (a 60 W light bulb level, for example, scaled by surface area).

Heating in a magnetic coil is given by $I^2*R$, where I is the root mean square current and R is the resistance of the device (at the frequency of operation). While the operating current I will be constrained by the required magnetic field for a given coil, the resistance may be altered in order to control heating. The most direct way to reduce heating is to use a conductor with a larger cross sectional area, which will reduce the resistance. The problem with using just a larger cross section conductor, however, is that a single conductor having a large cross section is difficult to use in fabrication of the coil as it is difficult to bend and form such a conductor without damage. Using a larger cross section conductor also has the disadvantages of requiring more space and inhibiting portability. Coils that have a dense coverage of conductor on a physical surface may be constrained in the enlargement of conductor along the surface; coils that use particular manufacturing methods or materials may be constrained in the enlargement of the conductor perpendicular to the surface.

In general, the resistance of a coil made of wire or cable will be limited if larger wires cannot be selected because of pattern density on the coil winding surface, and because wires have generally similar cross sectional radii in all directions, that will limit the wire size perpendicular to the surface. In another example, coils that are made from copper sheets (in which a conductive path has been cut) can be designed to use as much of the surface as possible for conductor size, but will be constrained as to the thickness of the copper because of radial bending and other manufacturing limitations. In both cases a coil, wound on a surface, may be limited with respect to the minimum resistance that can be achieved.

In accordance with the present invention, this limitation can be overcome by structuring the coil in multiple layers. In one embodiment, two layers are placed substantially in parallel with respect to each other, and the two layers generate substantially the same magnetic field. The two coil layers can be connected electrically in series or in parallel as best suits the drive power available in the system. Because the fields of the two coil layers can reinforce each other, each of the two layers can be driven by ½ the current required to generate substantially the same magnetic field using a conventional, single-layer coil. The magnetic fields produced by the individual layers aggregate so as to produce the desired magnetic field. In this case the heat generated by the coil (i.e., by the two layers together) is reduced by half [(I/2)^2*R+(I/2)^2*R)=I^2 R/2]. This offers a substantial improvement in heat reduction. The use of two layers can reduce the heat generated by a coil in half, and the use of more layers would have a corresponding reduction in heat generated by the device. Various embodiments of the LFMS device generate 13 W of power, using two layers. Because of this low level of heat, these embodiments do not require a cooling system. This design is well suited for use in treatments in which a significant amount of heat, e.g., 100 W, may be generated without using a two-layer coil.

The use of double layers in a coil allows for two methods of connecting the coils in a circuit—in parallel electrical connection or series electrical connection—in order to share a single power source. Because the coil layers are adjacent to each other and provide the same shape of field, there is some choice available in design that can be used to reduce costs or improve performance, in terms of the power requirements. A magnetic coil is substantially an inductor, and can provide a given magnetic field using an amount of current. Electric circuit theory informs us that the rate of change in current, multiplied by the inductance, determines the required driving voltage. This rule applies to the inductive voltage; there is an additional term depending on the current that describes the resistance.

For LFMS, the rate of change of the magnetic field, scales the electric field strength induced by the coil. The magnetic field is proportional to the electric current. As a result the required rate of change of the electric current directly affects system design. Electric field theory also informs us that for a given continuous current density design for a coil, the inductance increases as the square of the number of "turns" of wire used to approximate the required continuous current density ("turns" in the sense of the density of discrete conductors, perpendicular to the current direction, that are used to approximate a continuous current density). When two layer patterns that are similar are placed together and connected, their net inductance includes an additional interaction term usually equal to twice the mutual inductance of the two patterns, which is about the sum of the inductances of two layers. Finally, electric circuit theory informs us that the current in a coil that is required to produce a given field is inversely proportional to the number of "turns" used in the implementation of the continuous design.

Thus, for a single layer coil, halving the number of turns used in design will double the required current and cut the required voltage by ½ (a factor of ¼ for the change in number of turns but a factor of two for the double rate of change in current from doubled peak current). If a second layer is added in series, with the same number of turns as the first layer, then the fields of the two layers will add. This means that in order to achieve the same field as with one layer, each layer can use half the current and double the voltage as a single coil. This is equivalent to the original single layer but a double layer coil allows a reduced resistance and a freedom to choose the power configuration.

The second layer can be configured in parallel with the first layer to produce a coil that has the same total current and voltage requirements as a single layer coil producing substantially the same magnetic field, but with reduced heating because the current in each of the two layers is about half the total current. It can also be configured in series. Either configuration may be advantageous for power supply choice and cost and will depend on available amplifier choices, and the requirements of the LFMS system.

Structure of a Two-Layer Coil

In general, the coil preferably includes a casing and conductor forming the coil winding. The coil may also include a bonding agent. In one embodiment the conductor is solid wire. The conductor may also be stranded wire or litz-wound wire. In another embodiment the conductor is a cut solid copper plate, using for example water-jet or mechanically cutting techniques, which may be curved for ease of construction. The copper plate may be disposed on a substrate, such as plastic or, e.g., an FR4 substrate. The casing encompasses the conductor.

In one embodiment, the LFMS system is based on a magnetic coil mounted in a coil assembly and driven by an amplifier; the amplifier waveform is controlled by a controller which is in turn run by a computer program on a computer.

Figure 3A:
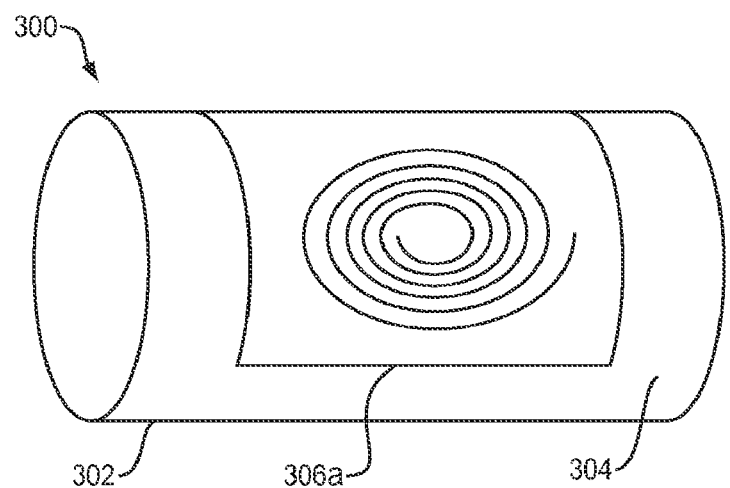
FIGS. 3A-3G schematically illustrate various embodiments of two-layer coils.
Figure 3B:
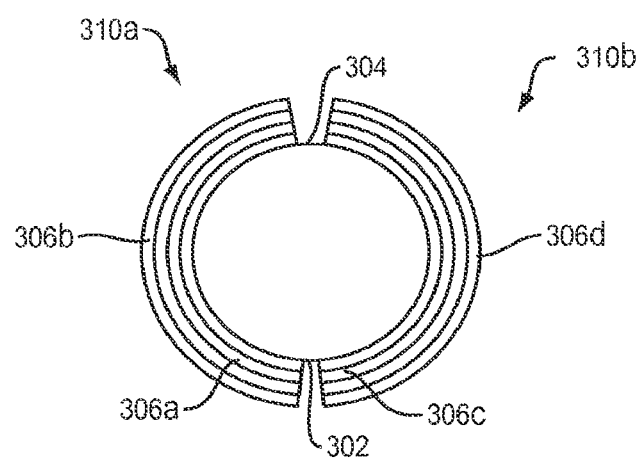
Figure 3C:
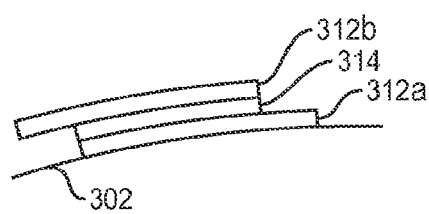
Figure 3D:
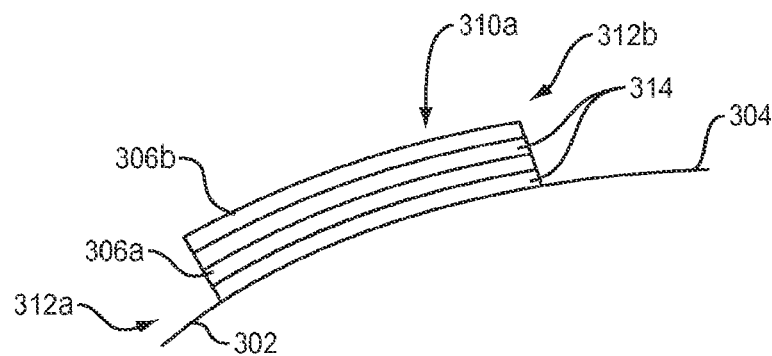
Figure 3E:
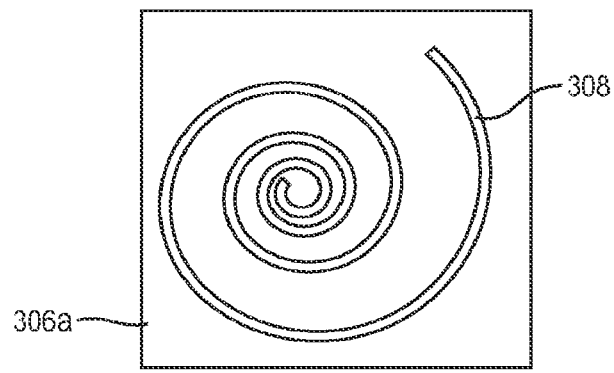

With reference to the embodiments illustrated in FIGS. 3A-3G, a coil assembly is based on a 14 inch diameter plastic cylinder 102 which is about 19 inches long. The plastic cylinder 302 is the mounting surface 304 for the coil 300 that includes four copper plates 306a-306d. Each copper plate is about ⅛ inch thick, and has a spiral cut 308 made therein, as shown in FIG. 3E. The spiral cut 308 may extend to the edge of the plate 306a. The four copper plates form two elements 310a, 310b of the coil 300; each element includes two plates. In the first element, one copper plate is placed on the surface 304 of the plastic cylinder 302, forming the first layer 312a of the first element 110a. Another plate is placed on top of the first layer 312a, forming the second layer 312b of the first element. The first layer 312a has an interior surface in contact with the surface 302 and an exterior surface. The second layer 312b also has an interior surface and an exterior surface, and the interior surface of the second layer is separated from the exterior surface of the first layer by a distance, as described below.

The first and the second layers (e.g., plates or wound wires) are aligned with each other, i.e., the two layers are of about the same size and shape and the second layer substantially overlaps the first layer, as illustrated in FIGS. 3B and 3D. In some embodiments, however, the area of one of the two layers may be larger than that of the other. Alternatively, or in addition, the shapes of the two layers may be different (e.g., layer one may be rectangular and layer two may be ovular). In some embodiments, the layers may only partially overlap with each other, i.e., they may be aligned with an offset, as shown in FIG. 3C.

Figure 3F:
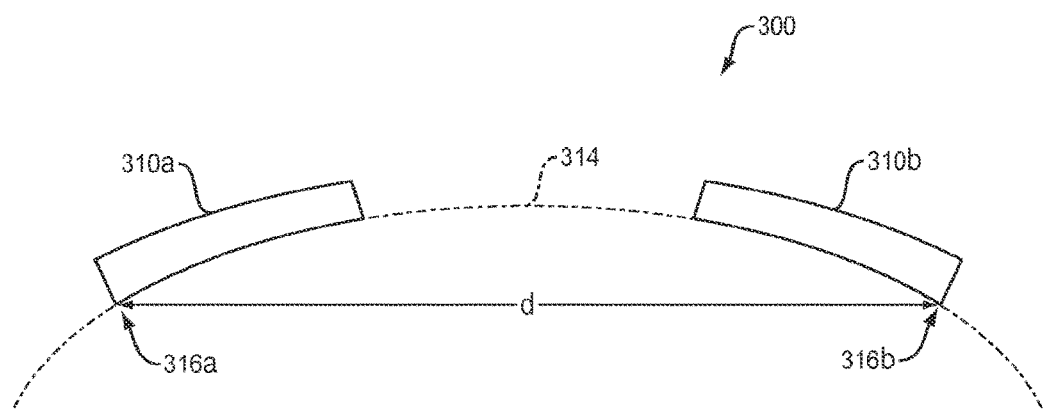

In some embodiments, the plates (layers, in general) are not disposed on a mounting surface such as the surface 304 of the plastic cylinder 302. The inner surfaces of the coil elements, however, form portions of a single surface. A cross-section of that single surface, as depicted in FIG. 3F, includes an arc 314 corresponding to the one or more coil elements 310a, 310b. A distance "d" between two ends 316a, 316b of the arc 314 is in the range of about 5 inches up to about 36 inches. This enables subjecting a person's head or a portion thereof to an electric field induced by the coil 300. In some embodiments, the inner surfaces of the coil elements form portions of different surfaces that are spaced apart by a substantially constant distance.

Each plate (i.e., layer) in each coil element is preferably mounted on a substrate 314 that serves as a mechanical mount and as an electrical insulator between the coil windings and any adjacent objects. A spacer in addition to or instead of the substrate 314 may also be used. The copper plates are not planar; instead, they have a curved surface as depicted in FIGS. 3B-3D, such that the surface of the plastic cylinder 302 and the two plates are nearly concentric. The thickness of the substrate 314, or spacer, or both typically determine the distance between the layers 312a, 312b such that the use of a 1/16 inch thick FR4 substrate, in accordance with one embodiment, results in a 1/16 inch distance between these layers. This distance is preferably substantially constant. In other embodiments, the distance can be about 5 mm, 1 cm, etc. The distance between the two layers need not be substantially constant; instead it may vary with a tolerance of about 5%, 10%, 25%, etc. In various embodiments, materials other than FR4, such as any flexible insulator (e.g., polyester, polyamide, etc.) may be used as a substrate. In some embodiments, a combination of various materials may be used while in yet other embodiments, each layer may be separated by air alone.

Figure 3G:
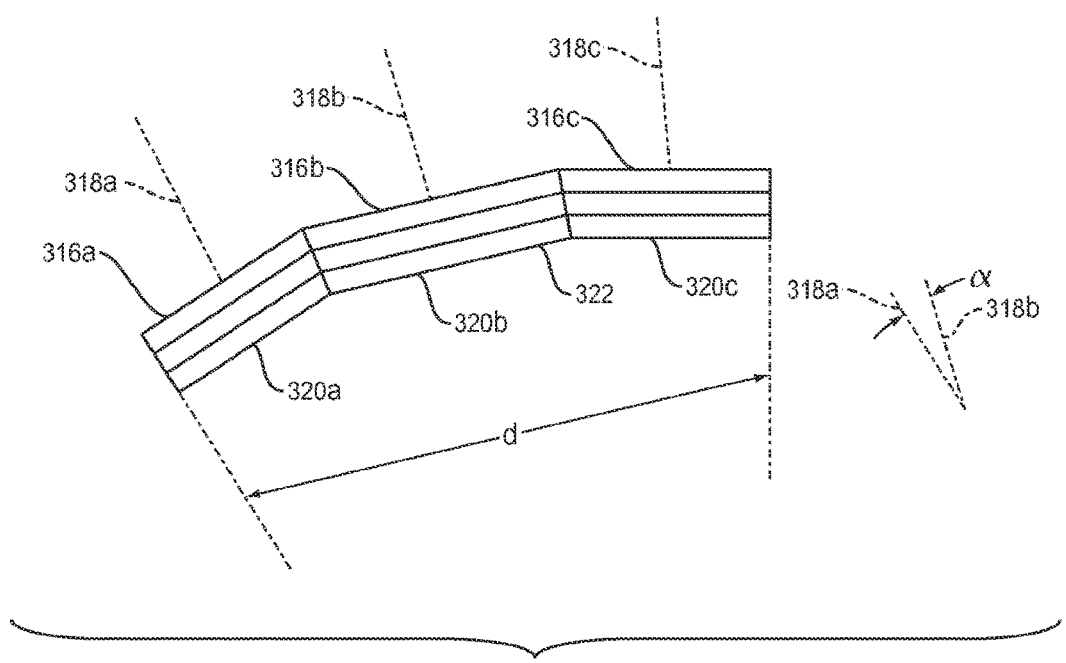
Figure 10:
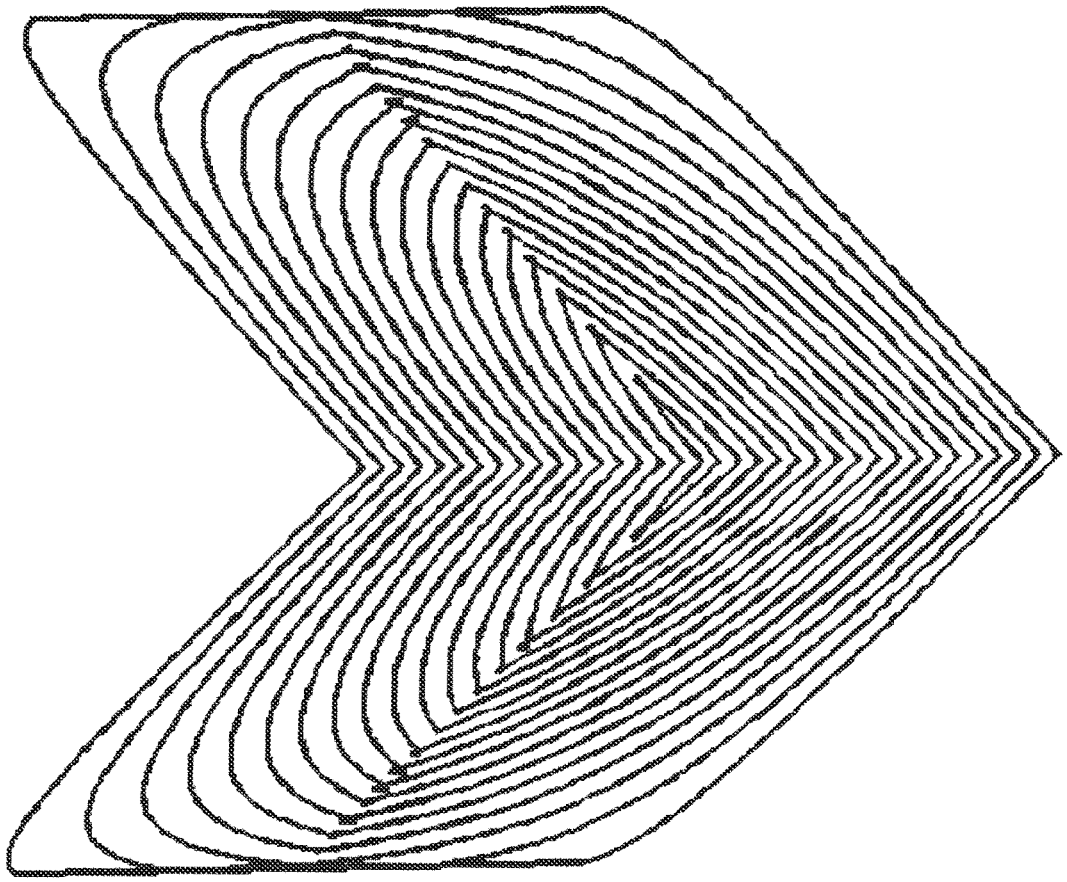
FIG. 10 depicts a coil element disposed in a bent arrangement.

As also illustrated in FIG. 3G, in some embodiments, instead of using one plate as a layer of a coil element, the layer is formed using two or more segments 316a-316c, i.e., planar or curved segments, that are disposed at an angle with respect to each other. Specifically, a surface normal 318a of one layer segment 316 is not parallel to a surface normal 318b of another layer segment 316; instead, the two surface normals 318 are at an angle α with respect to each other. For example, the coil element shown in FIG. 10 includes two rectangular segments at an angle. The angle between two segments is generally 45° up to 180°, but segments at an angle less than 45° are also contemplated. Each of the segments 316a-316c in a layer includes coil windings disposed thereon or spiral cuts made therein. The size and shape of the segments and the angles are selected such that the distance between the corresponding segments of two layers of a coil element (e.g., segments 316a and 320a, 316b and 320b, and 316c and 320c) is substantially constant, as shown in FIG. 3G. A cross section of the segmented surface thus formed is a segmented arc 322. The distance "d" between two ends of the arc 322 is in the range from about 5 inches up to about 36 inches.

A spiral cut in each plate forms a coil winding in each layer, having an inner and outer connection; there are about 35 winding turns in each spiral cut. In general, the number of winding turns is determined by the current density that is required to produce the target field and by the choice of power source to be used to drive the coil. A given current density can be provided by a high number of turns with a smaller current or by a lower number of turns with a higher current. In each case the voltage required of the power source changes to reflect the current and the coil impedance. High and lower numbers of turns result in higher and lower (respectively) inductance. The resistance of a coil depends on several factors; for a wire coil, more turns means a longer wire (increased resistance) and perhaps an upper limit to wire size (in the case of tightly spaced turns). In a copper plate coil the same factors apply, with the exception that the resistance will reduce with the number of turns directly due to the fact that the entire turn-to-turn spacing will be filled with copper. Thus a design choice in the number of turns can be made to accommodate different power sources and conductors. A different concern in selecting the number of turns is the uniformity and smoothness of the fields. In general, the spacing can be chosen to be less than the distance between the coil and the head of a subject, so that the magnetic field in the region in which the head is disposed does not vary greatly. Thus, the choice of the number of turns may also be influenced by a requirement for smooth fields. The second element of the coil is formed similarly as the first element. The two elements together span about 180 degrees, i.e., about half the circumference of a cross section of the plastic cylinder 302, and the length of the copper plates 306a-306d, which is also the length of each element, is about 14 inches. Smooth fields may be desired in order to induce similar magnitude of electric fields throughout regions of the brain, rather than focusing the fields in one localized portion of the brain, in order to efficiently provide treatment to these brain regions.

The relative direction of currents in each coil element determines the distribution of the fields. This direction may be described using vectors. A positively rotating current (right hand current) is one that rotates counterclockwise when viewed in a direction against the outward normal of the surface. A negatively rotating current (left hand current) has the opposite rotation, clockwise when viewed against the outward normal of the surface. Using this vector terminology, coil elements of this coil design that are adjacent in either azimuth or in longitudinal position have the opposite polarity. This corresponds to the approximate current density solution presented above.

The plates (i.e., layers) can have any suitable planar shape such as a square, rectangle, circle, oval, etc. As described above, the layer can be planar or may have a curved surface. In one embodiment, the plates 312a-312d are 21 inches long and 19 inches wide. The two-element coil 300 can be used to treat the entire brain of a human subject, but layers having smaller dimensions can be used if only a portion of the brain or head is to be treated.

The exact pattern of the spiral cut is determined based in part on a mathematical design so that current supplied to the spiral of each layer produces a magnetic field with a desired spatial distribution, i.e., the "target field." The coil layers are driven by electrical current simultaneously, and the magnetic fields from each layer add to form a final target field.

The electrical interconnection and rotational directions of the spiral cut in each of the four layers are configured in order to provide a mechanically robust assembly and to reduce peak voltages and electric fields between the coil layers and elements. Each spiral cut forms an inner end/connection and an outer end/connection. The rotational direction of the current in each element is determined by the desired target field. The spiral direction of the conductor in a layer typically depends on the rotational direction of the current and on the configuration of connections to the spiral (i.e. current into the inner or outer connection).

In one embodiment, the spiral cuts of the first layer of each element rotate in a clockwise direction, as viewed from outside the cylinder, traveling outward from the center. The spiral cuts of the two outer plates, i.e., the second layer in each element, are counterclockwise when observed in the same manner. In each coil element, the center of the plate that forms the first layer is electrically connected to the center of the adjacent plate forming the second layer of that element. The outer ends/connections of the second layers in each coil element are connected together with a wire/bus bar. The outer ends/connections of the plates forming the respective first layers in each coil element are connected to the power source. The centers of the plates are located on the sides of the cylinder. Thus, all plates are electrically connected in series, and the current flows as follows: in the first element, current enters from the outer end of the first-layer plate and travels to the center; connects to the center of second-layer plate and travels to the outside of the spiral through the outer end of the second-layer plate to the bus bar. From the bus bar, the current enters the second element from the outer end of the plate forming the second layer in the second element; to the center of that layer; then to the center of the plate forming the first layer, and then through the spiral to the outer end of plate forming the first layer (in the second element), and back to the power supply via the amplifier. This connection and spiral direction scheme results in a constructive addition of the fields from the first and second layers of each element, and enables the reduction in heat generated, through the use of the two adjacent layers and the reduced electrical resistance that they afford.

The current drive for the coils is provided by a standard audio frequency amplifier, either linear, switching, or other suitable design. The amplifier is controlled by a waveform that is supplied by a controller. This controller may take the form of a output card mounted in a standard computer that plays a pre-recorded waveform, or it could be the output of a special sequencing card such as the Arduino that plays and repeats segments of the full waveform. In other embodiments, the two layers may be electrically connected in parallel and/or the two coil elements may be electrically connected in parallel. In embodiments having more than two layers and/or more than two coil elements, various combinations of series and parallel connections that minimize the heat generated by the coil while producing the desired magnetic field are feasible, and are contemplated.

The amplifier may be driven in current mode or in voltage mode for reasons of electrical safety; in the case of a voltage mode drive, standard pre-emphasis modifications to the desired waveform may be performed to accommodate the impedance of the coil.

Figure 4:
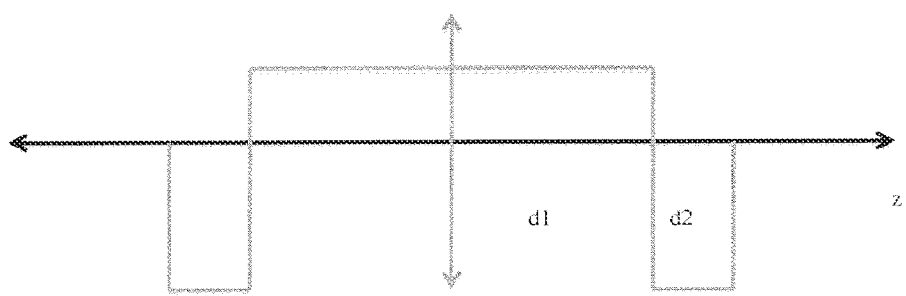
FIG. 4 shows an envelope function graph.
Figure 5:
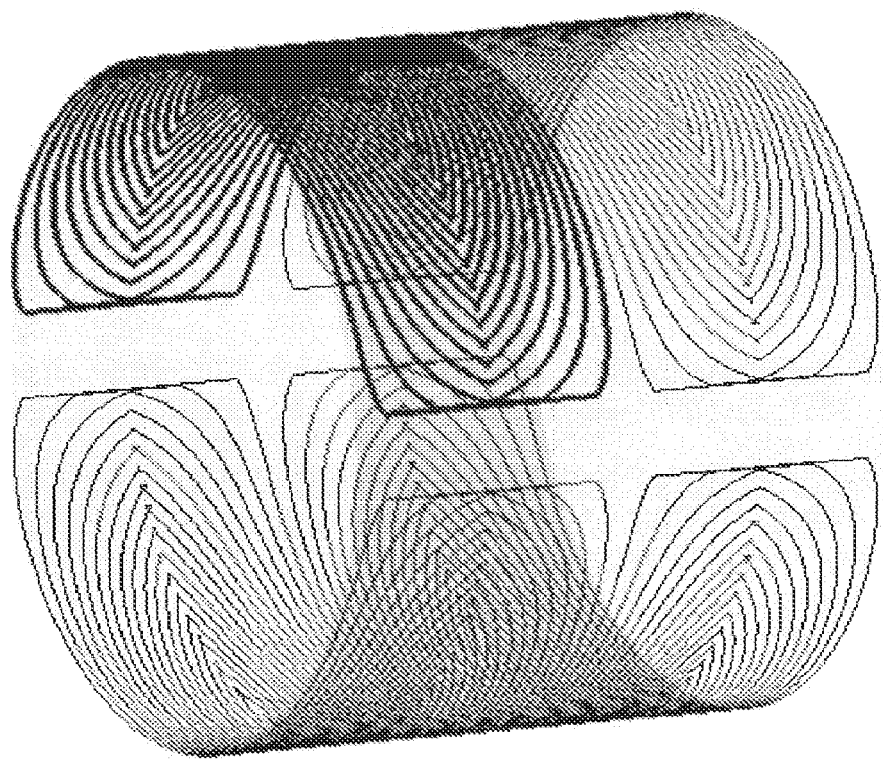
FIG. 5 shows a full coil (e.g., a coil having four elements)

FIG. 4 depicts a typical envelope function used to modulate the target field spatially, in the longitudinal direction as shown in FIG. 2, in order for the target field method to produce finite and practical electromagnetic fields. FIG. 5 shows a four element coil. The symmetry of the coil in azimuth and along the z direction results in a coil with four independent coil elements, each of a spiral form that spans between 90 degrees and 180 degrees of the circumference of the coil. The coil elements may be connected in series, parallel or combinations thereof. The number of turns in each coil element may be varied as long as the total current crossing each unit length of the surface remains the same (i.e., halving the turns requires doubling the current per turn).

In an LFMS system using a half coil, in which the envelope function is truncated, only one d1 and d2 parameter set (shown in FIG. 4) is implemented. The d1 and d2 parameters are set to be equal at the radius of the half coil (about 7 inches) in order to optimize the field strength. A substantially shorter coil for this radius would result in a weaker field, and would require a denser wire pattern, due to the mathematical requirements of projecting target fields into space (see "A target field approach to optimal coil design," R. Turner J. Phys. D: Appl. Phys. 19 L147 (1986)). A much longer coil would provide a satisfactory field but would have an unnecessarily large inductance, requiring unnecessary amounts of power for the system. The aspect ratio of length~diameter is an optimum ratio that balances these concerns.

In one embodiment, the radius of the coil is 14 inches, a size that will accommodate the patient's head comfortably, and with enough room that the field of vision for the subjects is not impeded when the head is placed in the treatment position, at the end of the coil. This aids in patient comfort during treatment.

The target field region is an area wherein the magnetic fields exist to induce the desired electric fields in the subject. The target field region of the coil in FIG. 5 is in the center of the coil, defined as a volume centered at the intersection of the first and second radial directions of the coil cylinder (e.g., the first and second radii 202, 204 in FIG. 2), and in the plane separating the elements longitudinally.

Figure 6:
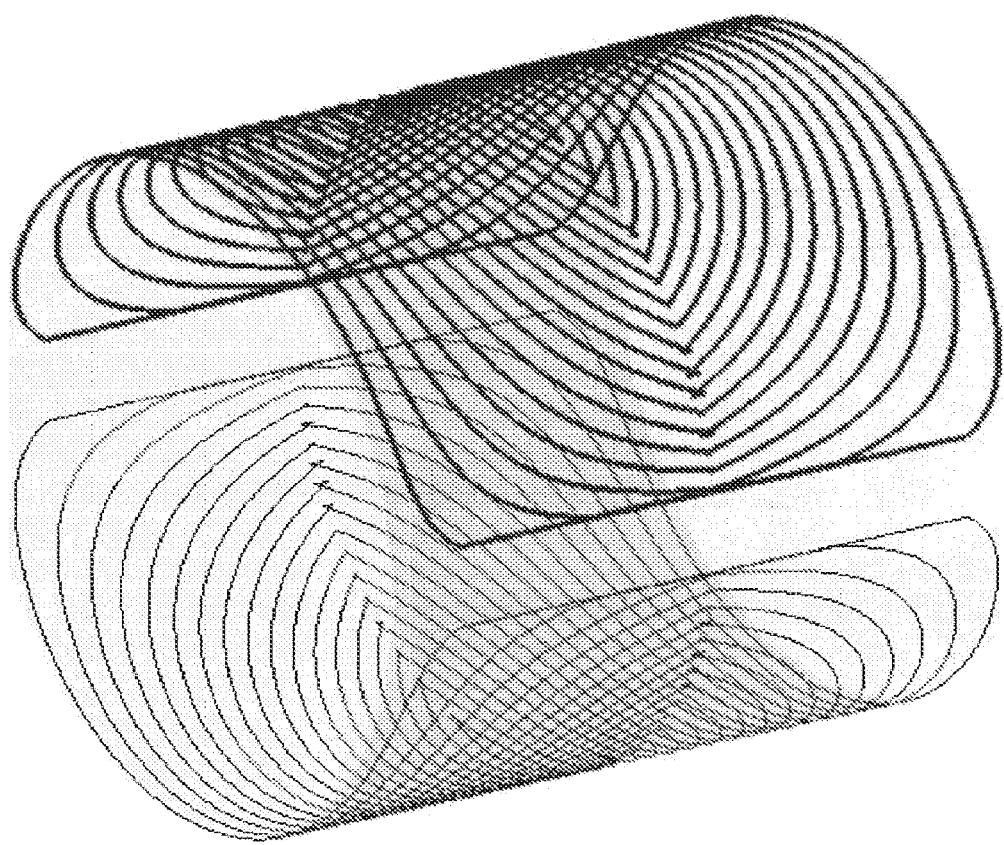
FIG. 6 shows a half coil (e.g., with only two coil elements)

FIG. 6 shows a half coil with only two coil elements. A full coil, described with reference to FIG. 5, has four elements. This coil will have substantially similar target treatment regions at the end planes of the coil elements, providing a coil which is shorter and more patient friendly. The shorter coil allows subjects to have only a portion of their heads enclosed by the coil rather than having the coil positioned on their shoulders. This may relieve symptoms of claustrophobia or other subject discomfort caused by limited vision or confinement. This may have particular value in treating depressed subjects.

Figure 7:
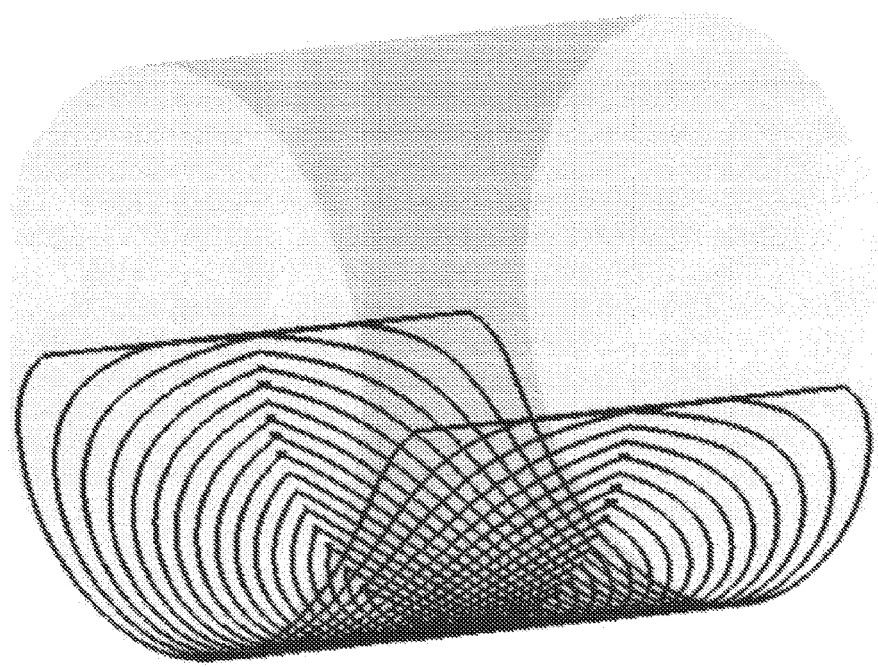
FIG. 7 shows a quarter coil (e.g., with only one coil element)

FIG. 7 shows a quarter coil with only one coil element. This coil will have even more substantial deviation from the ideal target field, but the basic symmetry is still present in the resultant field and is sufficient for LFMS.

In one embodiment the coil includes elements that are oriented such that the axis of the loop components is along a horizontal direction, collinear with the axis of the coil (also referred to as the X direction). In another embodiment, the coil is rotated about the axis of the cylindrical form so that the axis of the loop elements is vertical and orthogonal to the X direction (also referred to as the Y direction). In this way the distribution and direction of the fields of the coil are rotated about the axis of the cylindrical form. Coils providing equivalent fields may be constructed using spherical or semi-spherical boundaries.

In some embodiments, the electric field induced by the magnetic field of the coil has substantially uniform field strength over a region in air, having an area of at least about 2 $cm^2$, e.g., 4 $cm^2$. A person receiving treatment may be disposed relative to the coil such that at least a part of the cortical surface of the person's brain is located in that region where there electric field strength is substantially uniform. Such an electric field may be induced using a coil having broadly distributed coil windings, e.g., windings that have a regular distribution over the area of the cortex to be treated. If the cortex is 3 cm away from the coil, a guide is that the wires should be spaced less than 3 cm apart, over the target area, in order to provide uniform electric field over the area subtended by the coil area.

The optional housing for the coil is made of a non-conductive, insulating material, such as plastic, wood, fiberglass or carbon fiber. In an alternative embodiment the portion of the housing that is not between the subject and the coil can be made of a conductive material, such as copper, in order to provide an electromagnetic shielding layer to contain the external field of the device. The housing encompasses the coil providing protection for the coil, subject and users of the coil.

Some embodiments of the LFMS system include an extra feature, in addition to the half-coil design and projected target field area, that provide for patient comfort. For example, the coil is mounted on a sliding platform. This allows a patient to place his or her head on a head rest while the coil is several inches away—avoiding the possibility of hitting the head while positioning. After the patient is comfortable, the coil is slid into place. The head of the patient is inside only the first few inches of the coil, which may provide a significant reduction in patient anxiety. The coil of the LFMS device can be mounted on a movable platform because the coil generates the required magnetic field independently of a magnet, and hence, need not be located inside a magnet or affixed thereto.

Coil Design Based on the Target Field Method

The target field method (see "A target field approach to optimal coil design," R. Turner J. Phys. D: Appl. Phys. 19 L147 (1986)) is a method of determining the physical location of a set of electrical conductors so that a desired magnetic or electric field will be produced when current is run through them. This method is used to design MRI gradient and shim coils and any other coils that require fields with a specific field distribution.

The basic properties of electromagnetic fields are employed to generate such fields in a variety of ways. In particular, the fields within a closed volume may be generated by a larger number of current patterns outside the volume. These current patterns are chosen to occur on desired geometric surfaces, such as planes, cylinders, spheres, or other surfaces of other shapes. Given a surface, and a target field, the current on the given surface that will produce the given target field can be uniquely defined.

Some surface shapes are more suited for use as surfaces for current that may produce a desired target field. A surface that fully encloses a target field volume can most easily produce that target field (with respect to maximum current density values and amount of stored field energy). The lesser a target field area enclosed by the current bearing surface, the more difficult the required current pattern (with respect to maximum current density magnitude and amount of stored energy) to generate that target field. But in general a variety of coil shapes are used to provide a desired target field that exists near the coil, outside the enclosed volume of the coil. A spherical target field, for example, can be obtained by currents on a cylinder, on a half cylinder, on a sphere, on portions of a sphere, or on planes and plane segments near the target field.

In general practice target fields are defined to exist inside an implicit finite volume enclosed by the coil generating the field. While an unbounded extension of the target field outside the enclosed volume typically results in an impractical current density (with respect to maximum current density values and amount of stored energy), a practical design is feasible by allowing the field to tend to zero outside the enclosed volume as quickly as possible. Thus, the field achieved by a coil with the actual target region (which is outside the enclosed volume of the coil) may differ from the specified field (which defines the filed to be inside the enclosed volume) used for the coil design. The degree to which the achieved and specified fields may differ is determined by the needs of the particular application. For example, a 10% difference is significant for MRI gradient coils; for brain stimulation, however, a 25% change in target field can be tolerated, because the induced electric fields themselves generally change according to the properties of a subject's head.

Therefore, in various embodiments, the coil may include two or more elements, each of which is preferably disposed in a non-overlapping manner on a single surface, or in partially overlapping manner on substantially concentric surfaces that are spaced apart. The single or the substantially parallel surfaces may be partially spherical, elliptical, arched, curved, straight (i.e., flat), or bent. As described herein, "disposed on a surface" means a coil element disposed substantially in contact with the surface such that the coil element has about the same shape as that of the surface upon which the coil element is disposed. The coil element may be directly in contact with the surface or another material such as a substrate may intervene between the surface and the coil element.

In one embodiment, the coil is constructed from a single conductor element having a single layer. In an alternative embodiment the coil is constructed from two or more conductor layers as described above. These conductors may be electrically connected in series or in parallel. As stated above, the conductors may be formed using a wound solid cable or a wound stranded cable. The conductor may also be formed by carving a pattern in a metal plate or film. The multiple layers may be able to reduce power consumption and cooling requirements of the coil.

The target electric field may extend over the entire brain or regions within the brain. In one embodiment, the target electric fields may affect the cortical areas of the brain that regulate mood and behavior, such as frontal regions. In another embodiment the target electric field may affect subcortical areas of the brain that regulate mood and behavior, such as the basal ganglia and thalamus.

The electric field outside of the coil's enclosed volume can be useful for treatment. In the case of an elliptic or cylindrical coil, the electric field may extend beyond the edge of the coil in the longitudinal direction. The extension of the electric field may allow positioning of the greater portion of the subjects head outside of the coil. Such a positioning enables the inducement of electric fields within the head of a subject with a reduced risk of claustrophobia, and improves the comfort of the subject.

Spherical Coils

Figure 8A:
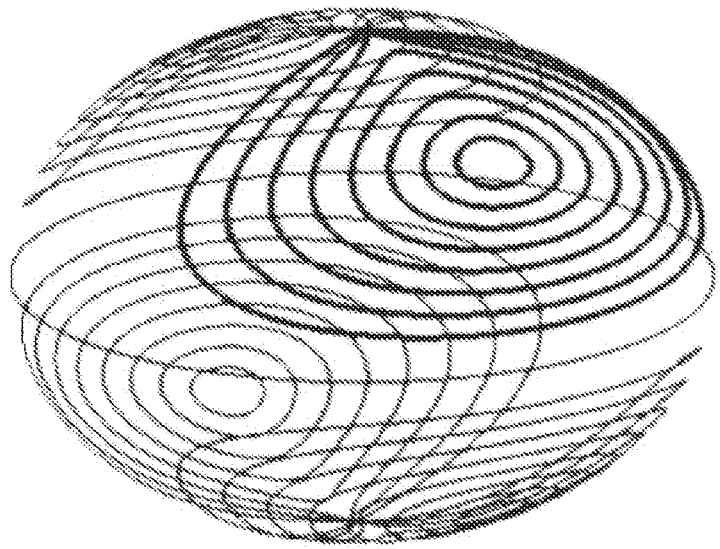
FIGS. 8A-8C depict coil elements disposed in a substantially spherical arrangement.
Figure 8B:
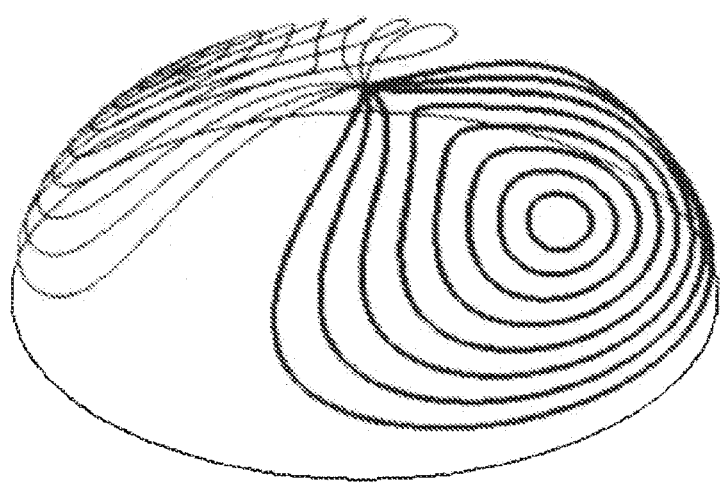
Figure 8C:
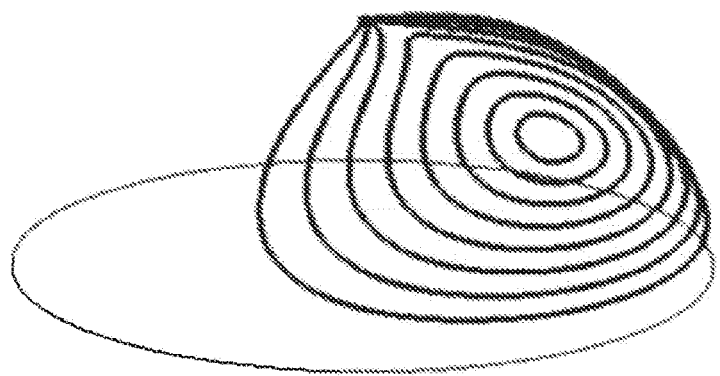
Figure 9A:
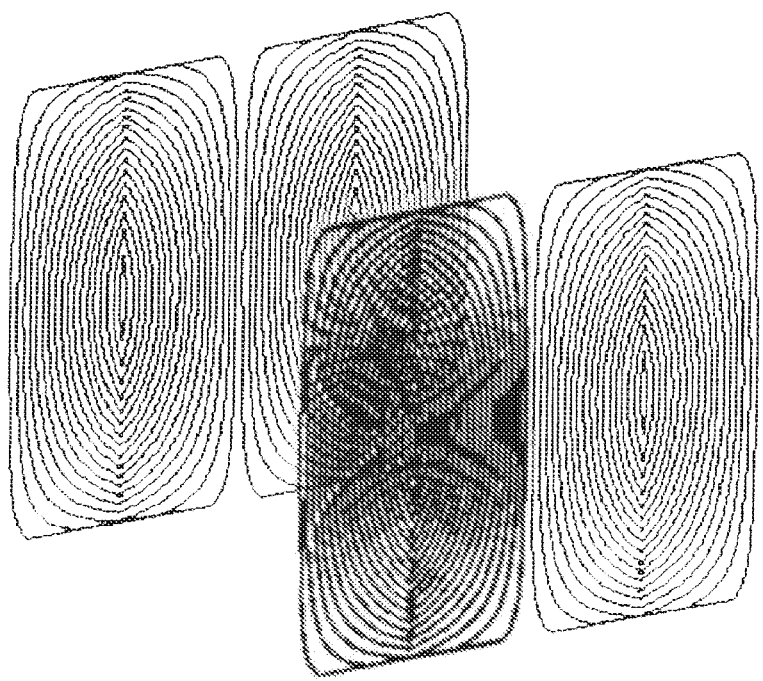
FIGS. 9A-9C depict coil elements disposed in a substantially flat arrangement.
Figure 9B:
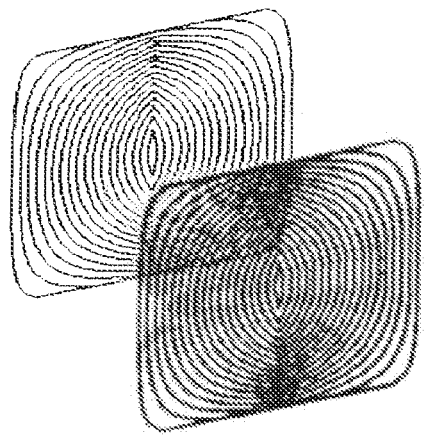
Figure 9C:
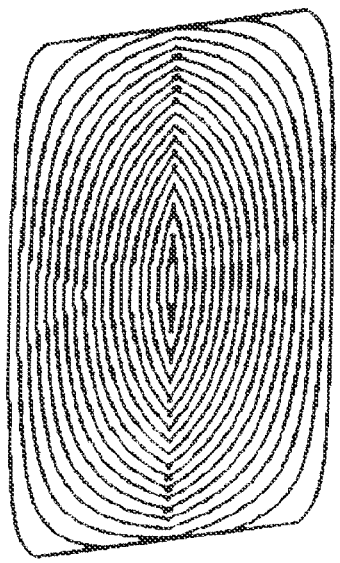

As illustrated in FIGS. 8A-8C, the fields described above may be accomplished with the use of coils that form a spherical shape or mounting surface. Spherical coils that produce the LFMS fields in their interior have the solutions $$\vec{B}_-(\vec{r}, t) = G(t)\{\hat{r}2r\sin\theta\cos\theta\cos\varphi + \hat{\theta}r(\cos^2\theta - \sin^2\theta)\cos\varphi - \hat{\varphi}r\cos\theta\sin\varphi\} = G(t)\{\hat{r}r\sin2\theta\cos\varphi + \hat{\theta}r\cos2\theta\cos\varphi - \hat{\varphi}r\cos\theta\sin\varphi\}$$

$$\vec{B}_+(\vec{r}, t) = G(t)\left\{\hat{r}\frac{R^5}{r^4}\sin2\theta\cos\varphi - \frac{2}{3}\hat{\theta}\frac{R^5}{r^4}\cos2\theta\cos\varphi + \frac{2}{3}\hat{\varphi}\frac{R^5}{r^4}\cos\theta\sin\varphi\right\}$$

$$\vec{J}(t, \theta, \varphi) = -\frac{1}{\mu}\frac{5}{3}G(t)R\{\hat{\theta}\cos\theta\sin\varphi + \hat{\varphi}\cos2\theta\cos\varphi\}$$

In these equations, some of the parameters of the spherical shape include the radius of the sphere, r, a polar angle of a coil segment on the sphere, theta, and the azimuth angle of the coil segment, phi. The number, size, and/or current patterns of coil elements are determined according to one or more of these parameters based on the equations above such that a desired target field is achieved while limiting the current density to an acceptable level so that the coil does not generate excessive heat. There are four non-overlapping current patterns in the spherical coil, and thus four coil elements, in this design. For practical use only half the coil with two elements disposed in azimuth may be in use in order to accommodate human subjects efficiently. These two coil elements can be referred to as spherical coil quadrants because there are four elements in a full spherical coil.

Although a complete sphere cannot be used to treat a human subject's head, a half sphere cut along the plane theta=90 can provide substantially the same field, with somewhat less efficiency, that can be compensated for by supplying more current to the coil. The hemispherical coil, shown in FIG. 8B, has resemblance to the cylinder coil in that the azimuth currents follow a cos(theta) behavior. If this coil is aligned with phi=0 to the L or R of the subjects head, a field substantially the same as for the X gradient can be produced, with electric fields induced in the cortex along the A-P direction. If the hemisphere is rotated so that phi=0 is in the A or P direction, then electric fields induced in the cortex may follow a L-R pattern and cross between hemispheres. A single quadrant element depicted in FIG. 8C may be used following the same pattern in any position in order to focus on a particular area of the cortex.

In general, a spherical coil is more comfortable to a patient as it is not as close to the patient's head as the conventional cylindrical coil would be. A spherical coil, however, typically needs more current relative to a cylindrical coil to induce an electric field of about the same strength as that induced by a cylindrical coil. This is at least in part because unlike while using a cylindrical coil, when using a spherical coil the patient's head is often further away from the enclosed volume of the coil. For treatment/enhancement of brain function the required field strength is not as high as that required for imaging, and two quadrant and single quadrant spherical coils can be used to induce the desired electric field.

The hemispherical coil depicted in FIG. 8B has two coil elements; each is centered at points 180 degrees apart in azimuth, and subtends substantially 180 degrees in its extent. A sufficient field of the same pattern may be produced if a coil element is placed centered at an angle of 0, 90, 180, or 270 degrees and subtends between 90 and 180 degrees as shown in FIGS. 8A-8C.

Coils that are focused on the PFC regions may use one or more elements that subtend only 45-90 degrees and that are placed less than 180 degrees apart, e.g., 90 degrees apart, may be used to increase efficiency. These coils follow the azimuth symmetry of the basic (i.e., cylindrical) LFMS coil in that azimuth current follows a substantially cos(phi) pattern.

Flat and Angled Coils

With reference to FIGS. 9A-9C and FIG. 10, coils providing equivalent fields may be constructed using plane and angled plane geometries. The same relationship between the rotations of the current densities as in cylindrical coils is preserved in these coils. These coils are electric current solutions of the same basic LFMS fields that have been produced on different boundaries.

Pulse Generator

The electronics module includes an amplifier, and a waveform generator. The waveform generator provides a sequence of electrical pulses (i.e., voltage pulses) to the amplifier, which amplifies them and provides current pulses to the coil elements. Those current pulses typically generate a magnetic field, as described above. The current required by the coil elements may also be delivered by controlling voltage across the coil leads. A voltage waveform required to produce a desired current waveform (i.e., a current pulse sequence) in the coil elements can be computed based on the known impedance of the coil. In one embodiment the waveform generator is a general-purpose programmable computer. In another embodiment the waveform generator is a purpose-built electric circuit. The waveform generator is able to provide the waveforms described in this specification.

In one embodiment, the electrical pulses generated by the waveform generator are continuous alternating trapezoid pulses. These produce similar continuous, alternating trapezoid variation of the magnetic field generated by the coil. The corresponding induced electric field may include square pulses that occur during the trapezoid ramps, alternating in sign, and with no field during the generally flat segments of the trapezoid. In one embodiment, the electric pulses includes bursts of 512 trapezoids at a time, with zero-to-peak ramp time of about 128 microseconds, and generally flat segments of the trapezoid in a duration of about 768 microseconds. There is a waiting period of about 1.5 seconds in between a sequence of pulses, and the treatment lasts for approximately 20 minutes. Treatment times may be increased up to the tolerance of the subject and may be as short as 1 minute.

In one embodiment the electric field is delivered as a train of substantially unipolar pulses with pulse duration in the range of 50 microseconds to 10 milliseconds. The individual pulses in this train may either alternate, or maintain the same polarity within the pulse train. Specifically, a unipolar pulse is a pulse having continuous values that are all either only greater than zero, or continuous values that are all only less than zero. A single pulse does not have continuous values that are both greater than and less than zero. Two consecutive pulses, separated by an interval of substantially zero value, may however have different polarities.

Figure 11:
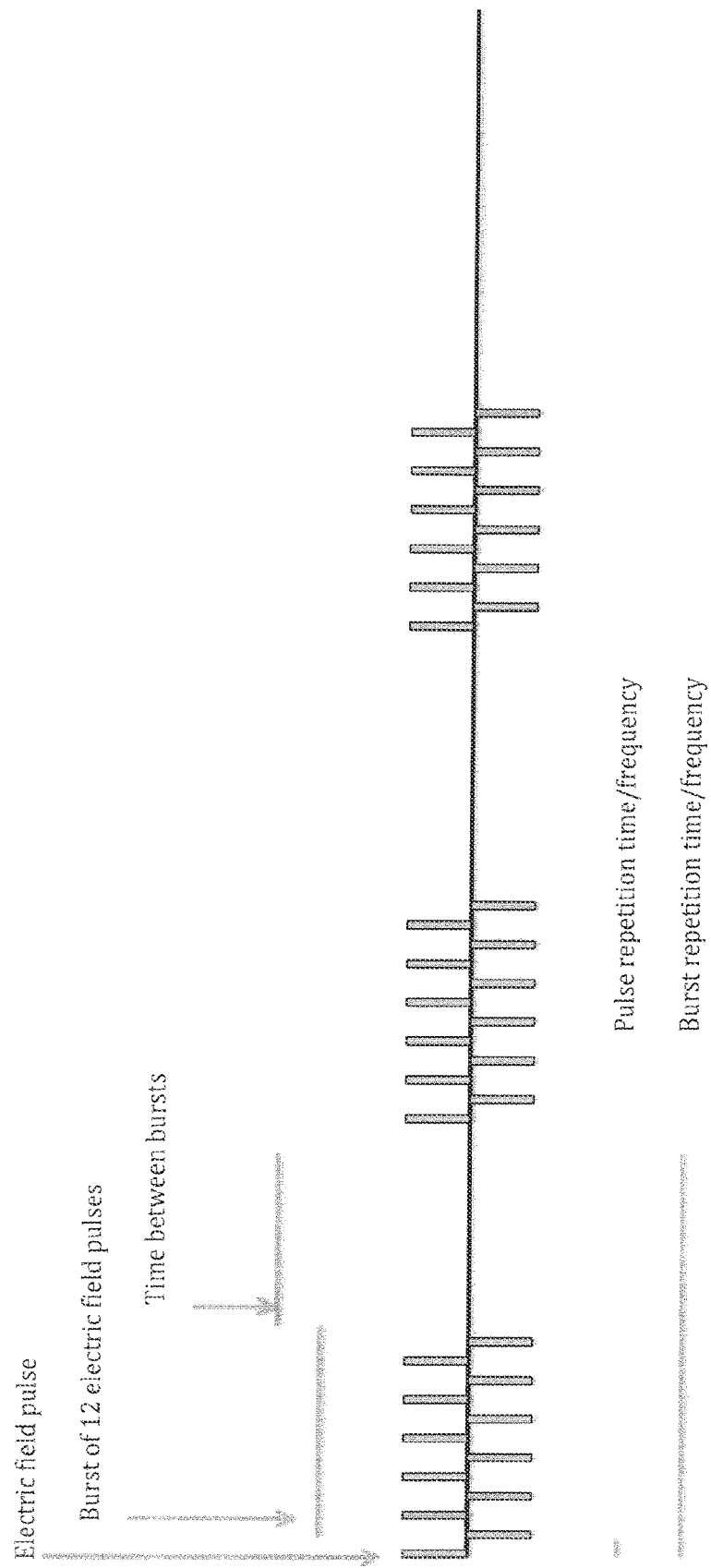
FIG. 11 shows a square pulse pattern with 3 bursts of 12 square pulses each.

A general pulse pattern is shown in FIG. 11, which shows a square pulse pattern with 3 bursts of 12 square pulses each. In one embodiment the pulses are separated by substantially no field. The pulses may have alternating polarity and may have the same absolute magnitude.

Figure 12:
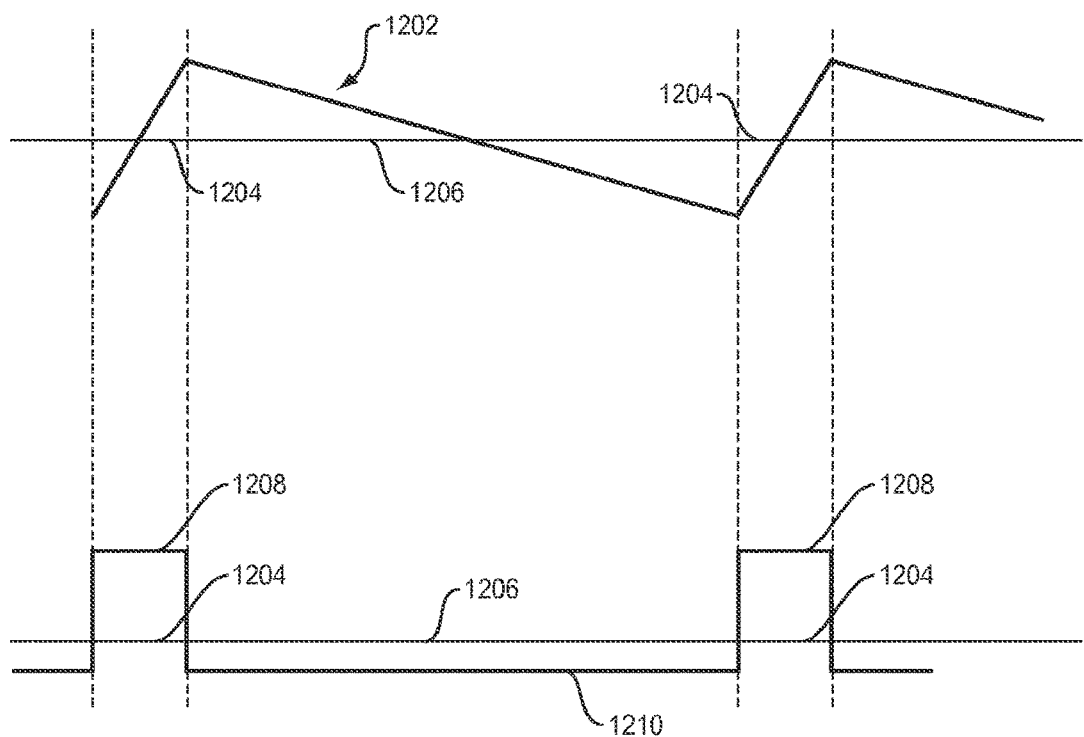
FIG. 12 depicts a "zero net integral" pulse pattern.

As depicted in FIG. 12, in one embodiment there are long periods of small opposite sign/polarity electric field periods between the pulses in a way that has substantially no net integral, but that continues to provide pulsed behavior. This can be achieved by configuring the pulse generator such that the magnetic field 1202 rises at a first rate during a first interval 1204. For example, the first interval 1204 is 0.25 ms long, and the magnetic field rises from about −30 Gauss up to about +30 Gauss during that interval, i.e., at a rate of about 234 Gauss/ms, Then, during a second interval 1206, the pulse generator is configured such that the magnetic field decreases at a second, substantially smaller rate. For example, the second interval 1206 is 0.75 ms long, and the magnetic field 1202 decreases from about +30 Gauss down to about −30 Gauss during that interval, i.e., at a rate of about 80 Gauss/ms, which is substantially smaller than the rate 234 Gauss/ms. It should be understood that the strengths of the magnetic field and the lengths of intervals described above are exemplary. Other embodiments may employ weaker or stronger magnetic fields, e.g., −50 to +50 Gauss, −20 to +20 Gauss, −20 to +50 Gauss, etc. The first interval may be shorter or longer such as 0.1 ms, 0.2 ms, 0.5 ms, etc., and the second interval may also be shorter or longer such as 0.5 ms, 1 ms, etc. An electric pulse 1208 having a magnitude greater than zero (e.g., 0.5 V/m, 0.7 V/m, 0.9 V/m, etc.) is generated when the magnetic field rises rapidly during the first interval. An electric field 1210 of relatively low magnitude and negative polarity (e.g., −0.1 V/m, −0.2 V/m, etc.) is generated during the second interval, and that field has the effect of providing a negative reference point for the positive pulses 1208. Integrated over the first and second intervals 1204, 1206, the electric field has a substantially zero integral value, i.e., no net integral. The first and second intervals are repeated so as to form a series of pulses separated by relatively long periods of small opposite polarity electric fields. The frequency of these pulses is greater than about 100 Hz, and preferably about 1 kHz.

As depicted in FIG. 13, in one embodiment the pulses are sinusoidal pulses 802 that are delivered in a first interval 1304 of continuous pulses that are separated by a second interval 1306 of no pulses, similar to the burst embodiment. In this case a burst, i.e., a period comprising a pair of consecutive first and second intervals 1304, 1306, has a duty cycle of less than 100%. Within the first interval, the pulse generator configures the gradient magnetic field such that the amplitude of all of the sinusoidal pulses 1302 is substantially constant, e.g., about 0.5 V/m, 0.7 V/m, 0.9 V/m, etc. The variation in the amplitude of consecutive pulses may be less than 0.5%, 1%, or 5%. In some embodiments, the amplitude of the sinusoidal pulses in at least one or at least two subsequent bursts is also about the same as the amplitude of the sinusoidal pulses in the first burst. Continuous sinusoidal pulse trains may be employed for a more efficient delivery of the base frequency as long as the pulses are substantially identical (up to sign) in amplitude and form in order to provide a steady state stimulus. The frequency of the sinusoidal pulses is greater than about 100 Hz, and preferably about 500 Hz. In comparison to a series of alternating pulses that are delivered at 1 kHz, a 500 Hz sine pulse train achieves the same 1 ms spacing between peak electric fields as the separated pulses. In some embodiments, the duty cycle of the burst is 100%, i.e., the second interval is zero seconds.

Patient Positioning for Treatment

In one embodiment the coil and coil housing are positioned such that a subject would be in a lying position. In the case of an elliptic cylinder, the longitudinal direction would be horizontal. In another embodiment the coil and coil housing are positioned such that a subject would be sitting or standing. In the case of an elliptic cylinder, the longitudinal direction would be vertical. In another embodiment, the coil and coil housing are positioned with the longitudinal direction at an angle between horizontal and vertical.

The patient positioning module provides assistance for the placement of a subject for delivery of the magnetic fields. It may include: (i) a headrest; (ii) physical markers; (iii) visual positioning markings; and (iv) lasers.

The headrest provides support to the patient's head and/or neck. The headrest includes a shaped material, preferably a plastic to accommodate a cushion layer upon it. The cushion layer is preferably made of foam with a plastic, vinyl or other coating that can be easily cleaned. The headrest is preferably located in front of the opening of the coil or partially within the coil.

In one embodiment physical markers are provided. The physical markers may include rods, pins, or stereotactic frames. The physical markers provide guidance for positioning of the subject's head in the optimal position. For example a rod may be inserted from both the left and right of the subject, illustrating the optimal location of an aspect of the subject's anatomy, such as the temples.

In one embodiment visual positioning markings are provided. The visual positioning markings may be located on the coil housing, on the headrest. The positioning markings may include arrows, lines, or other markings that help align the patient's head with respect to the coil.

In one embodiment lasers are incorporated into the system. One or more laser points, lines or cross-marks may be employed. The lasers assist in positioning the patient's head with respect to the coil. For example, two laser lines may be employed, with one creating a line in the sagittal direction and the other creating a line in the axial direction. The intersection of these two lines would illustrate the location of a specific part of the subject's anatomy, such that when that area of anatomy is aligned with the lasers, the subject's head is optimally located with respect to the coil.

The control module allows the user of the system to control its operations. It includes: (i) a computer; (ii) software; (iii) a display; (iv) an input device. The software includes a user interface, control electronics, data acquisition and data storage functionality. The input device may be one or more of: a mouse, keyboard, track pad, button, joystick, microphone for accepting voice commands, or other input device as is known in the art.

A method is provided for the use of the system, wherein a subject is placed within or adjacent to the coil module, and wherein electric fields are delivered to the subject.

The system and method may be used for the treatment of psychiatric disorders, including depression, stress and anxiety, schizophrenia, PTSD, and OCD, or for the enhancement of brain function. In treating a patient, the system may be employed to induce a single series of electric fields or multiple series of electric fields. Multiple series of electric fields may be spaced apart in time.

Clinical Trial

Sixty-three patients who met DSM-IV criteria for either bipolar disorder (BPD, N=41) or major depressive disorder (MDD, N=22) and who had a score of 17 or greater on the 17-item Hamilton Depression Rating Scale (HDRS) were randomized to receive either LFMS or sham treatment. Subjects participating in the study (mean baseline HDRS score of 22.4±4.2) were on a stable regimen of antidepressant or mood stabilizing medications for at least 6 weeks prior to randomization. Most subjects were taking multiple medications. This study was a double blinded, randomized, sham-controlled investigation of the acute mood effects of a single 20-minute exposure to LFMS. The HDRS, the Visual Analogue Scale (VAS) and the Positive and Negative Affect Scale (PANAS) were used to assess mood and depression systems pre and post-treatment. In the VAS, the subjects are asked to "Place an X on the line in a place that represents how your mood is at this moment [0-10]".

The group of all subjects (n=63) showed improvement with LFMS treatment over sham treatment in all outcome measures. These results show two important results. First, the portable LFMS Device can replicate the immediate mood improvement observed in the original study that used an MRI system. Second, the effects can be observed in subjects with MDD as well as those with BPD Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system comprising:
   a pulse generator; and
   a magnetic coil comprising a first element, an inner surface of the first element forming at least a part of a spherical surface, the first element being in electrical communication with the pulse generator,
   wherein a parameter of the magnetic coil is selected such that the coil produces a gradient magnetic field proximate to a region at least partially enclosed by the spherical surface, the gradient magnetic field inducing an electric field in air up to about 50 V/m.

2. The system of claim 1, wherein the parameter is selected from the group consisting of a radius of the spherical surface, a polar angle of a coil segment, and an azimuth angle of the coil segment.

3. The system of claim 1, wherein the first element comprises a first layer having an interior surface and an exterior surface, and a second layer having an interior surface and an exterior surface, wherein the interior surface of the second layer is separated from the exterior surface of the first layer by a distance.

4. The system of claim 3, wherein a distance between all points of the interior surface of the second layer and all corresponding points of the exterior surface of the first layer is within a tolerance that is less than 25 percent of a median distance between the interior surface of the second layer and exterior surface of the first layer.

5. The system of claim 1, wherein the first element comprises a plurality of turns of a conductor, at least one pair of adjacent turns being spaced apart and the plurality of turns being distributed over the first element.

6. A system comprising:
   a pulse generator; and
   a magnetic coil comprising a first element, an inner surface of the first element forming at least a part of a spherical surface, the first element being in electrical communication with the pulse generator,
   wherein the magnetic coil comprises a second element, an inner surface of the second element and the inner surface of the first element forming separate portions of the spherical surface.

7. A method of treating a psychiatric disorder or enhancing brain function using system comprising,
   a pulse generator; and
   a magnetic coil comprising a first element, an inner surface of the first element forming at least a part of a spherical surface, the first element being in electrical communication with the pulse generator,
   the method comprising:
   supplying electric power to the magnetic coil via the pulse generator to produce a gradient magnetic field proximate to a region at least partially enclosed by the spherical surface, thereby inducing an electric field in air proximate to the coil; and
   disposing a subject relative to the magnetic coil such that at least a portion of the subject's head is located in a region where the electric field is induced.

8. The method of claim 7, wherein the psychiatric disorder comprises at least one of mood disorder, depression, stress and anxiety, schizophrenia, PTSD, and OCD.

9. The method of claim 7, wherein a position in which the subject is disposed is either a supine position or a seated position.

10. A method of treatment using an induced electric field, the method comprising the steps of:
    (a) controlling a pulse generator during a first interval to produce a gradient magnetic field using a coil, the magnetic field having a magnitude that increases at a first rate during the first interval;
    (b) controlling the pulse generator during a second interval that is substantially longer than the first interval, such that the magnitude of the magnetic field decreases during the second interval at a second rate substantially smaller than the first rate, such that an electric field having a magnitude greater than zero is induced in air during the first interval and an electric field of a negative magnitude is induced in air during the second interval, wherein an electric field integrated over a period comprising the first and second intervals is substantially zero;
    (c) repeating alternately steps (a) and (b); and
    (d) disposing a subject relative to the coil such that at least a portion of the subject's head is located in a region where the electric field is induced.

11. The method of claim 10, wherein a repetition of the electric field having a magnitude greater than zero forms a series of electric field pulses having a frequency of at least 100 Hz.

12. The method of claim 10, wherein the portion of the subject's head comprises at least a portion of cortical surface of the subject's brain.

13. The method of claim 10, wherein the treatment comprises enhancing brain function or treating a psychiatric disorder, the psychiatric disorder comprising at least one of mood disorder, depression, stress and anxiety, schizophrenia, PTSD, and OCD.

14. The method of claim 10, wherein a position in which the subject is disposed is either a supine position or a seated position.

15. A method of treatment using an induced electric field, the method comprising the steps of:
    (a) controlling a pulse generator during a first interval to produce a gradient magnetic field using a coil, wherein: the gradient magnetic field (i) induces a plurality of consecutive sinusoidal electrical pulses having substantially constant amplitude in air during the first interval, and (ii) has an absolute peak strength of at least 1 Gauss and at most 50 Gauss;
    (b) controlling the pulse generator during a second interval such that the gradient magnetic field induces an electric field of substantially zero magnitude in air during the second interval;
    (c) repeating alternately the steps (a) and (b); and
    (d) disposing a subject relative to the coil such that at least a portion of the subject's head is located in a region where the plurality of sinusoidal pulses is induced.

16. The method of claim 15, wherein a frequency of the consecutive sinusoidal pulses is greater than about 100 Hz.

17. The method of claim 15, wherein the portion of the subject's head comprises at least a portion of cortical surface of the subject's brain.

18. The method of claim 15, wherein the treatment comprises enhancing brain function or treating a psychiatric disorder, the psychiatric disorder comprising at least one of mood disorder, depression, stress and anxiety, schizophrenia, PTSD, and OCD.

19. The method of claim 15, wherein a position in which the subject is disposed is either a supine position or a seated position.

20. The method of claim 15, wherein the absolute peak strength is at least 5 Gauss.

21. The method of claim 15, wherein the absolute peak strength is at least 20 Gauss.

* * * * *